(12) United States Patent
Saines

(10) Patent No.: US 6,261,258 B1
(45) Date of Patent: Jul. 17, 2001

(54) HEMOSTATIC DEVICE FOR ANGIOPLASTY

(76) Inventor: Marius Saines, 4560 Admiralty Way, Suite 356, Marina Del Rey, CA (US) 90292

(*) Notice: Subject to any disclaimer, the term of this patent is extended or adjusted under 35 U.S.C. 154(b) by 0 days.

(21) Appl. No.: 09/304,254

(22) Filed: May 3, 1999

(51) Int. Cl.[7] .................................................. A61M 13/00
(52) U.S. Cl. .............................. 604/58; 604/57; 604/904
(58) Field of Search ................................. 606/213, 214; 604/57, 58, 82, 904, 385.17, 385.18, 14–18, 59, 60, 285–288, 235, 236, 247, 219

(56) References Cited

U.S. PATENT DOCUMENTS

| | | |
|---|---|---|
| 4,056,854 | 11/1977 | Boretos et al. . |
| 4,309,994 | 1/1982 | Grunwald . |
| 4,324,262 | 4/1982 | Hall . |
| 4,986,820 | 1/1991 | Fischer . |
| 5,129,882 | 7/1992 | Weldon et al. . |
| 5,195,980 | 3/1993 | Catlin . |
| 5,221,259 | 6/1993 | Weldon et al. . |
| 5,275,616 | 1/1994 | Fowler . |
| 5,292,332 | 3/1994 | Lee . |
| 5,320,639 | 6/1994 | Rudnick . |
| 5,391,183 | 2/1995 | Janzen et al. . |
| 5,443,481 | 8/1995 | Lee . |
| 5,527,292 | 6/1996 | Adams et al. . |
| 5,540,715 | 7/1996 | Katsaros et al. . |
| 5,649,959 | 7/1997 | Hannam et al. . |
| 5,797,899 | 8/1998 | Tilton, Jr. . |
| 5,810,810 | 9/1998 | Tay et al. . |
| 5,830,130 | 11/1998 | Janzen et al. . |
| 5,843,051 | 12/1998 | Adams et al. . |
| 5,844,087 | 12/1998 | Zimmermann . |

FOREIGN PATENT DOCUMENTS

| | | |
|---|---|---|
| 333 25 622 A1 | 1/1985 | (DE) . |
| 1173433 | 12/1969 | (GB) . |

OTHER PUBLICATIONS

"Tisseel® VH Fibrin Sealant", published in *Contemporary Surgery*, Dec., 1998 (Exhibit 19).

PCT Publication No. WO 95/08951 for PCT/US94/10993 by Hammerslag, published on Apr. 6, 1995.

Primary Examiner—Anhtuan T. Nguyen
Assistant Examiner—Kevin C. Sirmons
(74) Attorney, Agent, or Firm—Oppenheimer Wolff & Donnelly LLP

(57) ABSTRACT

A hemostatic device for sealing blood vessels, particularly for use in angioplasty comprises: (1) a barrel including: (a) a cylindrical portion; and (b) a terminal tapered portion, the terminal tapered portion being divided by at least one slot cut therein so that the tapered portion expands radially when force is applied to it; and (iii) an aperture at the narrow end of the terminal tapered portion; (b) a proteinaceous powder in the cylindrical portion of the barrel, the proteinaceous powder including at least one protein that promotes hemostasis in a blood vessel, the aperture in the terminal tapered portion being for flow of the proteinaceous powder; and (c) a plunger inserted into the barrel, the plunger including: (i) a narrow portion including therein means for guiding a guidewire; and (ii) a conical portion extending from the narrow portion so that, when the plunger is inserted into the barrel, the large end of the conical portion is located closest to the tapered portion of the barrel. The proteinaceous powder can be fibrin, thrombin, or fibrinogen. In use, the device is inserted into the tissue in the vicinity of an artery during the performance of angioplasty over a guidewire and leaves a plug in the tissue to seal the artery.

11 Claims, 2 Drawing Sheets

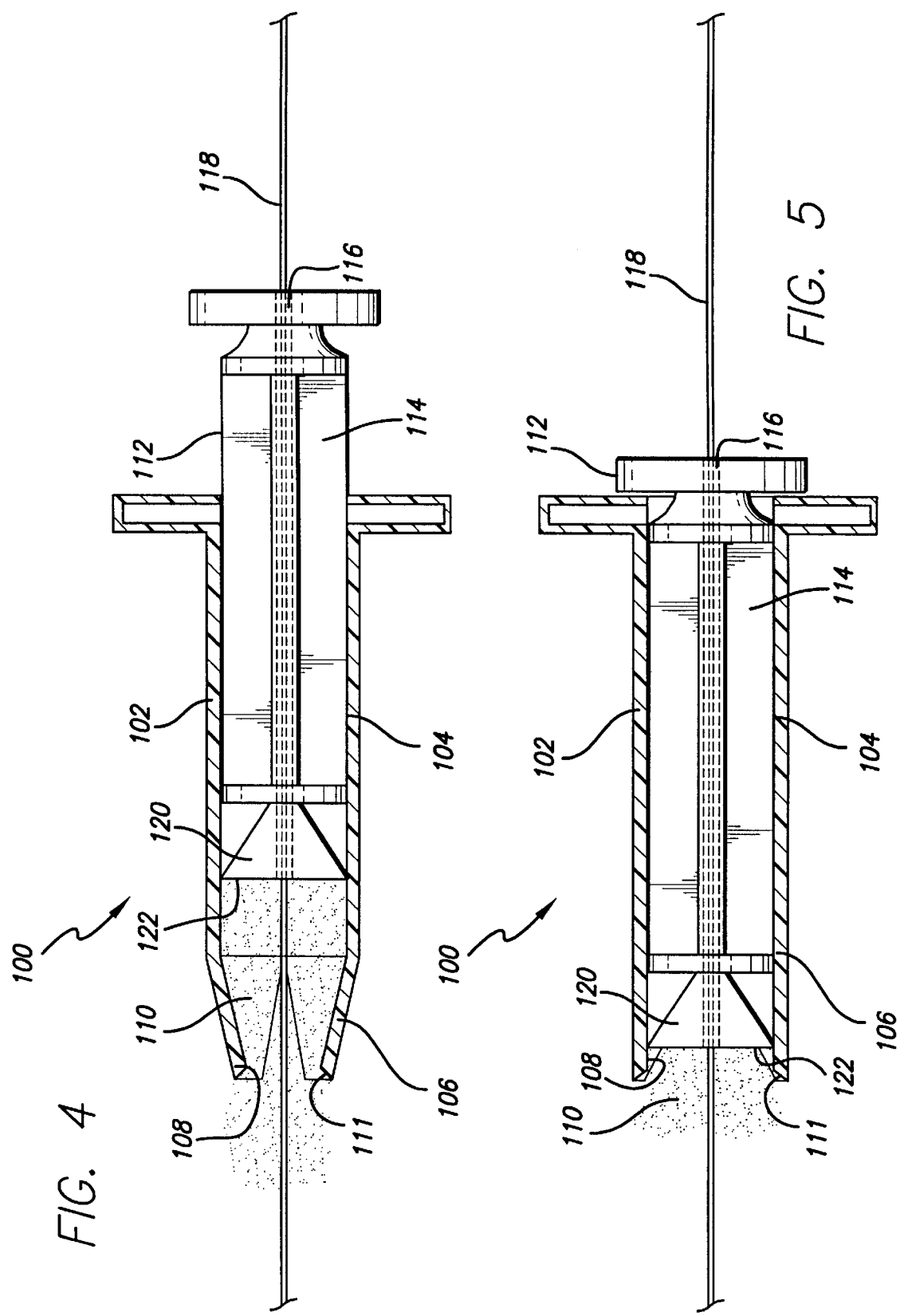

HEMOSTATIC DEVICE FOR ANGIOPLASTY

BACKGROUND OF THE INVENTION

The present invention is directed to a device for promoting sealing of blood vessels, particularly for use in angioplasty.

Angioplasty is an increasingly common surgical procedure, particularly for treatment of circulatory and cardiovascular disorders. Angioplasty involves the insertion of arterial catheters (which range between 5 F and 9 F). This requires the advancement of appropriate catheters over guidewires (which are in the range of 0.035 inches or 0.089 cm in diameter). At the present time, following removal of the catheter, bleeding at the arterial insertion site is stopped by application of a 5 pound pressure bag, use of manual compression, or application of a clamp to the limb of the patient for a period of time. All of these procedures are inefficient and painful. Furthermore, these procedures risk the occurrence of hematoma in the patient.

Among the devices that have been used for sealing arterial punctures such as those made during angioplasty are those described in U.S. Pat. No. 5,830,130, to Janzen et al., U.S. Pat. No. 5,527,292 to Adams et al., U.S. Pat. No. 5,843,051 to Adams et al., U.S. Pat. No. 5,649,959 to Hannam et al., U.S. Pat. No. 5,540,715 to Katsaros et al., U.S. Pat. No. 5,129,822, to Weldon et al., U.S. Pat. No. 5,221,259 to Weldon et al., U.S. Pat. No. 5,292,332 to Lee, and U.S. Pat. No. 5,443,481 to Lee, the disclosures of which are herein incorporated in their entirety by this reference.

Although these patents disclose a variety of approaches for sealing puncture wounds in arteries such as those generated by angioplasty, there is still a need for an improved approach to seal such puncture wounds. There is a need for a device that is painless and is more effective than existing devices and procedures for sealing such wounds. There is further a need for improved procedures and devices that reduce the risk of hematoma formation in such devices and procedures.

SUMMARY

An improved device for promoting hemostasis subsequent to angioplasty or other procedures that requires the puncturing of a blood vessel meets these needs. In general, the device comprises:

(1) a barrel including:
 (a) a cylindrical portion; and
 (b) a terminal tapered portion, the terminal tapered portion being divided by at least one slot cut therein so that the tapered portion expands radially when force is applied to it; and
 (c) an aperture at the narrow end of the terminal tapered portion;
(2) a proteinaceous powder in the cylindrical portion of the barrel, the proteinaceous powder including at least one protein that promotes hemostasis in a blood vessel, the aperture in the terminal tapered portion being for flow of the proteinaceous powder; and
(3) a plunger inserted into the barrel, the plunger including:
 (a) a narrow portion including therein means for guiding a guidewire; and
 (b) a conical portion extending from the narrow portion so that, when the plunger is inserted into the barrel, the large end of the conical portion is located closest to the tapered portion of the barrel.

Typically, the proteinaceous powder includes a protein selected from the group consisting of fibrinogen, fibrin, and thrombin.

Typically, the length of the barrel is about 1.5 cm and the diameter of the cylinder is about 0.3 cm. Typically, the means for guiding the guidewire is a channel in which the guidewire is inserted. Preferably, the channel has a diameter of about 0.5 mm.

Another aspect of the present invention is a method for sealing a blood vessel comprising:

(1) inserting the device of the present invention along a guidewire so that the terminal tapered portion enters the tissue in the vicinity of the blood vessel;
(2) pushing down the plunger to force the proteinaceous powder into the tissue in the vicinity of the blood vessel;
(3) removing the guidewire; and
(4) withdrawing the device from the tissue in the vicinity of the blood vessel to leave proteinaceous material in the tissue to assist hemostasis.

BRIEF DESCRIPTION OF THE DRAWINGS

The following invention will become better understood with reference to the specification, appended claims, and accompanying drawings, where: (to be inserted)

FIG. 4 is a side view of the device of FIG. 1 shown in a partially expanded configuration during its use; and FIG. 5 is a side view of the device of FIG. 1 at the conclusion of its use.

DESCRIPTION

An improved hemostatic device for angioplasty meets these needs. In general, the device is a modified syringe as shown in FIGS. 1–4. The device contains a proteinaceous powder that promotes clotting. As used herein, the term "powder" includes both amorphous powders and crystalline powders, including crystalline proteins.

Figure 1:
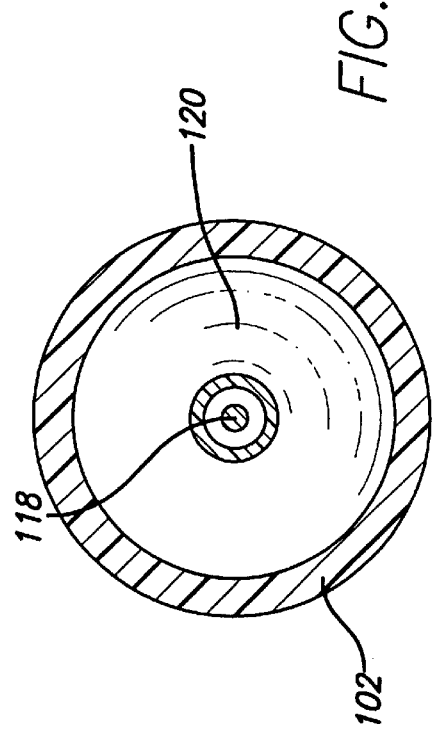
FIG. 1 is a side view of a hemostasis device according to the present invention.

The device is shown in FIG. 1. The device 100 includes a barrel 102. The barrel 102 includes a cylindrical portion 104 and a tapered portion 106. The tapered portion 106 is divided by at least one slot 108. The slot 108 is cut into the tapered portion 106 so that the tapered portion 106 expands radially when force is applied to it. More than one slot 108 can be used.

The cylindrical portion 104 of the barrel 102 also includes a proteinaceous powder 110. The proteinaceous powder 110 includes at least one protein that promotes hemostasis in a blood vessel. The proteinaceous powder 110 can also fill all or part of the cylindrical portion 104 of the barrel 102.

The tapered portion 106 of the barrel 102 also includes an aperture 111 for flow of the proteinaceous powder therethrough. The aperture 111 is at the narrow end of the tapered portion 106 of the barrel 102.

The device further includes a plunger 112 inserted into the barrel 102. The plunger 112 includes a narrow portion 114 including therein means 116 for guiding a guidewire 118. The means 116 is typically a channel in which the guidewire 118 can be inserted. The plunger 112 further includes a conical portion 120 extending from the narrow portion 114. The conical portion 120 extends from the narrow portion 114 in an arrangement so that when the plunger 112 is inserted into the barrel 102, the large end 122 of the conical portion 120 is located closest to the tapered portion of the barrel 102. The conical portion 120 helps to penetrate the skin and the subcutaneous tissue and helps to compress the inner material.

Typically, the proteinaceous powder includes at least one of the proteins fibrinogen, fibrin, or thrombin. A suitable preparation of fibrin is Tisseel fibrin sealant manufactured by Baxter Health Care Corporation. A suitable preparation of crystalline fibrinogen is a preparation known as Avitene produced by Med Chem Products, Inc.

Other proteins that stimulate clotting can be used.

Preferably, the length of the barrel is about 1.5 cm. Also, preferably, the diameter of the cylinder is about 0.3 cm. These dimensions can be adjusted as needed to adapt a device to deliver different volumes of proteinaceous powder and for use in different applications. The diameter of 0.3 cm was chosen based on the average size of the skin incision for arterial puncture. The height of 1.5 cm was based on the average distance between the skin and the arterial wall.

The diameter of the central channel in which the guidewire can be inserted is typically 0.5 mm. The diameter of this channel is chosen to accommodate a typical guidewire.

In use, the device 100 is inserted along the guidewire 118 so that the terminal tapered portion 106 of the barrel 102 enters the tissue in the vicinity of the blood vessel. The guidewire 118 is the guidewire that was used for the insertion of the catheter. The guidewire 118 is then removed and the plunger 112 is pushed down to force the proteinaceous powder 110 into the tissue in the vicinity of the blood vessel. After about 20 minutes, the device is withdrawn. This leaves proteinaceous material in the tissue in the vicinity of the blood vessel as a plug to assist hemostasis. A dressing can then be applied to the area. The dressing is typically a standard surgical dressing such as is normally used to close puncture wounds.

Figure 2:
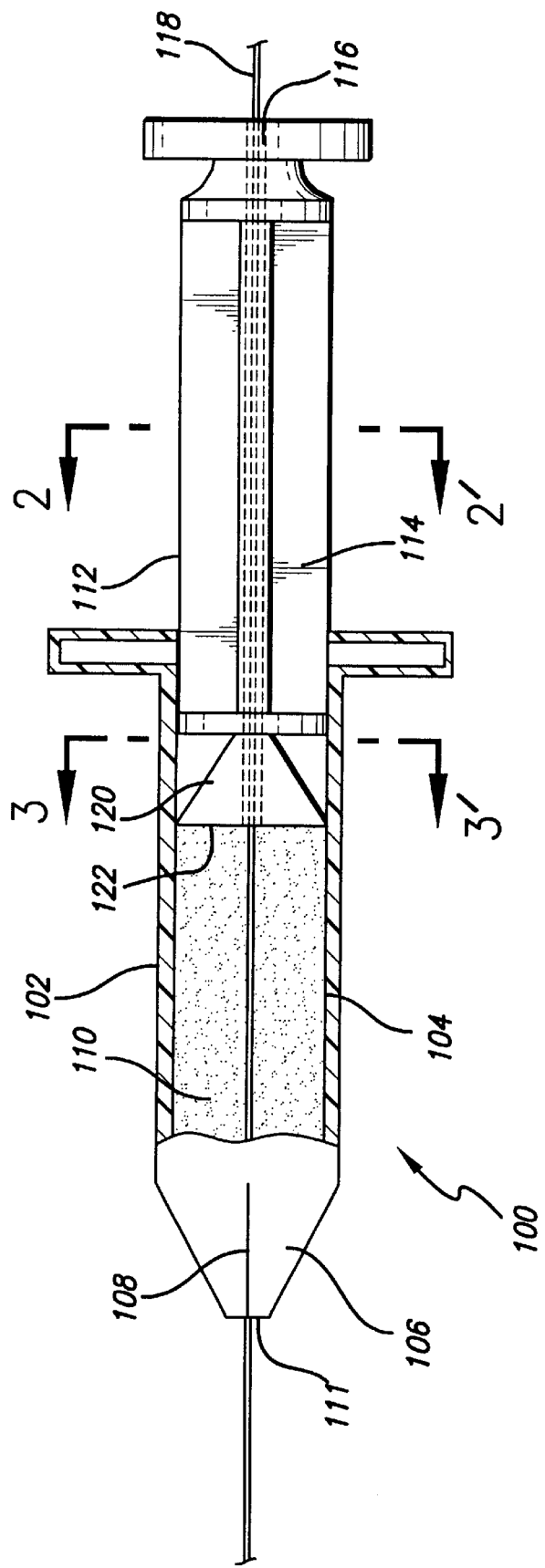
FIG. 2 is a cross-sectional view of the device shown in FIG. 1 along the line 2–2'.
Figure 3:
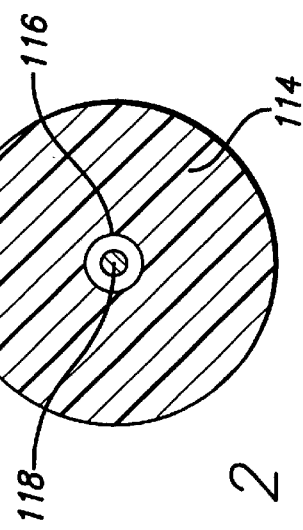
FIG. 3 is a cross-sectional view of the device shown in FIG. 1 along the line 3–3'.

Further details of the device are shown in FIGS. 2, 3, 4, and 5. FIG. 2 shows a cross-section of the device 100 along the line 2–2' in FIG. 1 toward the top of the barrel 102 showing the channel 116 for the insertion of the guidewire 118. FIG. 3 shows a cross-section of the device 100 along the line 3–3' through the conical portion 120 of the plunger 112.

FIG. 4 shows the device 100 in a side view at a stage where the terminal tapered portion 106 of the barrel 102 is expanding radially during use. FIG. 5 shows the device 100 after the plunger 112 has been pushed in to expel the proteinaceous powder 110.

ADVANTAGES OF THE INVENTION

The present invention provides an improved method of sealing blood vessels, particularly arteries, which have been opened as a result of surgical procedures such as angioplasty. The device provides more efficient sealing of these blood vessels, and reduces the pain suffered by the patient and the risk of hematoma formation. The device seals the hole rapidly by the insertion of material that forms a plug. The use of this device obviates a necessity for applying a five pound pressure bag, manual compression, or a clamp. The device can be adapted for the delivery of various volumes of clotting agents and for use in various applications.

Although the present invention has been described with considerable detail, with reference to certain preferred versions thereof, other versions and embodiments are possible. Therefore, the scope of the invention is determined by the following claims.

I claim:
1. A device for sealing a blood vessel comprising:
 (a) a barrel including:
  (i) a cylindrical portion; and
  (ii) a terminal tapered portion, the terminal tapered portion being divided by at least one slot cut therein so that the tapered portion expands radially when force is applied to it; and
  (iii) an aperture at the narrow end of the terminal tapered portion;
 (b) a proteinaceous powder in the cylindrical portion of the barrel, the proteinaceous powder including at least one protein that promotes hemostasis in a blood vessel, the aperture in the terminal tapered portion being for flow of the proteinaceous powder; and
 (c) a plunger inserted into the barrel, the plunger including:
  (i) a narrow portion including therein means for guiding a guidewire; and
  (ii) a conical portion extending from the narrow portion so that, when the plunger is inserted into the barrel, the large end of the conical portion is located closest to the tapered portion of the barrel.
2. The device of claim 1 wherein the proteinaceous powder includes a protein selected from the group consisting of fibrinogen, fibrin, and thrombin.
3. The device of claim 2 wherein the protein is fibrinogen.
4. The device of claim 2 wherein the protein is fibrin.
5. The device of claim 2 wherein the protein is thrombin.
6. The device of claim 1 wherein the length of the barrel is about 1.5 cm.
7. The device of claim 1 wherein the diameter of the cylinder is about 0.3 cm.
8. The device of claim 1 wherein the means for guiding the guidewire is a channel in which the guidewire can be inserted.
9. The device of claim 8 wherein the diameter of the channel is about 0.5 mm.
10. A method for sealing a blood vessel comprising:
 (a) inserting the device of claim 8 along a guidewire so that the terminal tapered portion enters the tissue in the vicinity of the blood vessel and so that the guidewire enters the channel;
 (b) pushing down the plunger to force the proteinaceous powder into the tissue;
 (c) removing the guide wire; and
 (d) withdrawing the device from the tissue in the vicinity of the blood vessel to leave proteinaceous material in the tissue to assist hemostasis.
11. A method for sealing a blood vessel comprising:
 (a) inserting the device of claim 1 along a guidewire so that the terminal tapered portion enters the tissue in the vicinity of the blood vessel;
 (b) pushing down the plunger to force the proteinaceous powder into the tissue;
 (c) removing the guidewire; and
 (d) withdrawing the device from the tissue in the vicinity of the blood vessel to leave proteinaceous material in the tissue to assist hemostasis.

* * * * *